United States Patent
Antognoli et al.

(10) Patent No.: US 7,273,954 B2
(45) Date of Patent: Sep. 25, 2007

(54) CATALYTIC METHOD FOR THE PRODUCTION OF CARBONYL COMPOUNDS

(75) Inventors: Franco Antognoli, Luzern (CH); Paul Rys, Zürich (CH)

(73) Assignee: Clariant Speciality Fine Chemicals (Deutschland) GmbH, Frankfurt Am Main (DE)

( * ) Notice: Subject to any disclaimer, the term of this patent is extended or adjusted under 35 U.S.C. 154(b) by 65 days.

(21) Appl. No.: 10/534,878

(22) PCT Filed: Nov. 14, 2003

(86) PCT No.: PCT/CH03/00749

§ 371 (c)(1),
(2), (4) Date: Dec. 12, 2005

(87) PCT Pub. No.: WO2004/043891

PCT Pub. Date: May 27, 2004

(65) Prior Publication Data

US 2006/0135817 A1    Jun. 22, 2006

(30) Foreign Application Priority Data

Nov. 14, 2002  (CH) .................................... 1916/02
Feb. 21, 2003  (CH) .................................... 0273/03

(51) Int. Cl.
*C07C 45/28*    (2006.01)
(52) U.S. Cl. ...................................... 568/320; 568/470
(58) Field of Classification Search ..................... None
See application file for complete search history.

(56) References Cited

U.S. PATENT DOCUMENTS 4,146,582 A * 3/1979 Maggioni .................. 568/309

FOREIGN PATENT DOCUMENTS

CH    609 318    2/1979

OTHER PUBLICATIONS

Khenkin et al. Oxygen Transfer from Sulfoxides: Oxidation of Alkylarenes Catalyzed by a Polyoxomolybdate.□□Journal of the American Chemical Society, 2002, vol. 124 (16), p. 4198-4199.*
Kornblum et al. A New and Selective Method of Oxidation. The Conversion of Alkyl Halides and Alkyl Tosylates to Aldehydes. Journal of the American Chemical Society, 1959, vol. 81, p. 4113-4114.*
*Pfitzner et al., "Sulfoxide-Carbodiimide Reactions. I. A Facile Oxidation Of Alcohols", j. am. Chem.. soc., 1965, pp. 5661-5670, vol. 87.

* cited by examiner

*Primary Examiner*—Sikarl A. Witherspoon
(74) *Attorney, Agent, or Firm*—Buchanan Ingersoll & Rooney PC

(57) ABSTRACT

The invention relates to a catalytic method for the production of aliphatic and aromatic carbonyl compounds with at least one aldehyde or ketone function, whereby said compounds can also comprise at least one aldehyde and ketone function. A starting material comprising at least one aliphatic- and/or aromatic-bonded functional group of formula (I), where $R^1$=H, alkyl or aryl, X=H, or a group which may be substituted by the sulphinyl group of a sulphoxide during the catalytic reaction, n=a whole number from 1 to 8, is oxidised in the presence of a sulphoxide and/or a sulphide and the presence of iron salts or redox pairs of iron/copper or silver/copper salts, by means of an oxidising agent with a redox potential of $E_o$>+2 V vs. NHE, whereby the sulphoxide or sulphide has a catalytic function. The method permits the production of carbonyl compounds, in particular, (poly)aldehydes and (poly)ketones with high selectivity, whereby the formation of alcohols and carboxylic acids, dimerisation products and other by-products is reduced to a minimum or essentially prevented. The final products obtained find application as important intermediates and final products.

20 Claims, No Drawings

CATALYTIC METHOD FOR THE PRODUCTION OF CARBONYL COMPOUNDS

This disclosure is based upon Swiss Application No. 1916/02, filed Nov. 14, 2002, Swiss Application No. 0273/03, filed Feb. 21, 2003, and International Application No. PCT/CH2003/000749, filed Nov. 14, 2003, the contents of which are incorporated herein by reference.

The present invention relates to a catalytic method for producing aliphatic and aromatic carbonyl compounds having at least one aldehyde or ketone function, and these compounds may also simultaneously have both aldehyde and ketone functions.

The aforementioned class of compounds includes significant products that in general are important intermediate or end products in various fields in the secondary and precision chemical industry.

Because of the importance of these products, many methods have already been proposed for their production. In some of these methods, alkyl or hydroxyalkyl compounds are used as starting materials.

However, in each case, the previously known methods are not widely usable, or are too complicated and expensive for industrial use.

Above all, they exhibit inadequate selectivity if the goal is to produce polyaldehydes or polyketones, that is, products that have a plurality of aldehyde or ketone functions in the same molecule.

If the previously known direct oxidation method is used for this, for instance as described in German Patent DE 2605678, Swiss Patent CH 609318, or German Patent DE 2944477, then the result is mixed-oxidized products, in which there are carboxyl, hydroxyalkyl and formyl or ketone groups, all combined in the same molecule.

For instance, in the production of 4,4'-oxybis(benzaldehyde) from 4,4'-oxybis(toluene) by the previously known direct oxidation methods, is at best 30 to 40 mol %.

It is also known that compounds with functional groups in accordance with formula I,

in which $R^1$ stands for hydrogen, alkyl or aryl, X stands for halogen, and n=1.

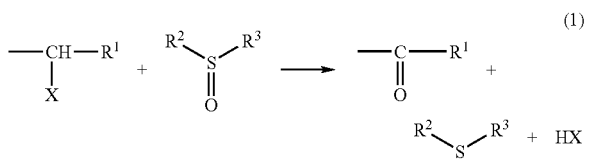

with sulfoxides, in which $R^2$ and $R^3$ stand for alkyl or aryl, react to form aldehyde or ketone groups and sulfides in accordance with reaction (1) (Kornblum et al, J. Am. Chem. Soc., 1959, 81, 4113).

Analogously, functional groups of formula I, in which X stands for hydroxyl, can be converted with sulfoxides into aldehyde or ketone groups and sulfides, if the hydroxyl group reacts with a previously formed derivative of sulfoxide, for instance formed as derivative with acid chlorides (Omura et al, Tetrahedron 1978, 34, 1651; Mancuso et al, Synthesis, 1981, 165), with dicyclohexylcarbodiimide (Pfitzner et al, J. Am. Chem. Soc., 1965, 87, 5661) or with acid anhydrides (Albright et al, J. Am. Chem. Soc., 1967, 89, 2416).

Finally, it recently has been learned that functional groups of formula I, in which $R^1$ stands for alkyl or aryl and X stands for hydrogen, react with sulfoxides and in the presence of polyoxomolybdates, also as in reaction (1) to form ketones and sulfides (Khenkin et al, J. Am. Chem. Soc., 2002, 124, 4198).

In all these cases, which are described by reaction (1), the stoichiometric quantity of the corresponding sulfides is created from sulfoxides.

The object of the present invention is to produce aliphatic and aromatic carbonyl compounds with high selectivity by a catalytic method.

This object is attained by a catalytic method in accordance with claim 1, in that the sulfide created is oxidized back into the corresponding sulfoxide continuously by addition of a suitable oxidant, so that the sulfoxide or the sulfide needs to be used only as a catalyst.

The method will be described below.

The starting material of this catalytic method is a compound which contains at least one (n≧1) functional group of formula I,

in which $R^1$ stands for hydrogen, alkyl or aryl, X stands for hydrogen or a group that can be substituted for the sulfinyl group of a sulfoxide during the catalytic reaction, and n stands for integral values between 1 and 8. This compound is oxidized in the presence of a sulfoxide and/or a sulfide in the simultaneously presence of iron salts or redox pairs such as Fe—Cu or Ag—Cu salts by means of an oxidant with a redox potential of $E_o$≧+2 V vs. NHE (normal hydrogen electrode), preferably by means of a persulfate salt. By means of the presence of the sulfoxide and/or of a sulfide, it becomes possible for the first time to produce the desired carbonyl compounds with very high selectivity; the formation of alcohols, carboxylic acids, dimerization products and other secondary byproducts is reduced decisively or essentially prevented.

This surprising phenomenon of the method of the invention can be ascribed to the intermediate formation of functional groups of formula II,

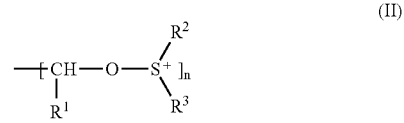

in which $R^1$ stands for hydrogen, alkyl or aryl, $R^2$ and $R^3$ stand for alkyl or aryl, and n stands for integral values between 1 and 8. As sulfoxides, dialkyl, alkylaryl or diaryl sulfoxides and mixtures of them are used. As sulfides, dialkyl, alkylaryl or diaryl sulfides and mixtures of them are used. The sulfoxides serve as acid transfer catalysts, which are either soluble in the reaction solution or are immobilized in a solid body made into a slurry (suspension) in the reaction mixture. The sulfides are either soluble in the reaction solution or are immobilized in a solid body made into a slurry in the reaction mixture.

The mole fraction of the sulfoxide and/or of the sulfide is 1 to 90 mol %, referred to the aldehyde or ketone function formed. A mole fraction of the sulfoxide and/or of the sulfide of 1 to 500 mol % can also be employed, if the kinetic reaction conditions for instance require this. Also in that case, the back-oxidation of the intermediately formed sulfide gains substantial significance.

The presence of a sulfoxide and/or of a sulfide in the reaction mixture can be accomplished in the most various ways.

The sulfoxide or the sulfide may be present alone or in a mixture of sulfoxides or sulfides. Moreover, the sulfoxide along with the sulfide may each be present individually or each in a mixture.

Surprisingly, the use of at least one sulfoxide and/or at least one sulfide in the reaction mixture leads to high selectivity.

Iron salts, alone or in combination with silver salts, serve primarily to split the persulfate to form the actual oxidant, that is, the sulfate radical anion. The use of a copper salt along with an iron salt or silver salt proves advantageous in the selective production of carbonyl compounds. For instance, the formation of dimerization products is effectively suppressed.

The method described may be performed by the gradual addition of the persulfate in the form of powder or in an aqueous solution, while stirring forcefully, to the previously placed starting material, which is dissolved in an inert organic solvent, in water, or in a mixture thereof. The sulfoxide and/or the sulfide may be present in this reaction mixture in dissolved form or in a slurry.

The most comprehensive conditions, which with respect to the starting material lead to the best selectivity, are adding a sulfoxide and/or a sulfide and the gradual addition of an aqueous solution of persulfate, while stirring forcefully, to a mixture of the starting material dissolved in water, with some proportion of organic solvent that is water-miscible. Especially suitable solvents are acetonitrile, methyl and ethyl alcohol (methanol and ethanol), acetone, acetic acid, dimethyl formamide, and acetamide.

Preferably, the proportion of organic solvent in the mixture with water is from 25 to 75%, referred to the water.

Examples of effective metal salts are the following:
a) all water-soluble iron salts, preferably sulfates, nitrates and acetates;
b) all water-soluble silver salts, preferably sulfates, nitrates and acetates;
c) all water-soluble copper salts, preferably sulfates, nitrates and acetates.

As a rule, the concentration of the iron salt or silver salt is from 0.005 to 10 mol %, referred to the starting material to be oxidized. The copper salt in the redox pairs is preferably used in a molar ratio of Fe:Cu or Ag:Cu of 0.1 to 3.

As a result, the oxidation is performed at a temperature of 10 to 100° C.

According to the invention, the method may also be based on a mixture of starting materials, and a similarly high selectivity for carbonyl compounds is attained.

With the catalytic oxidation method according to the invention, the selectivity of the carbonyl compounds produced, under optimized reaction conditions, can be increased considerably, sometimes to over 90%.

The present invention will be described in detail in terms of the examples below, without claiming to have described the industrial potential of the invention fully; in particular, the examples have in no way been optimized.

EXAMPLE 1

Production of 4,4'-oxybis(benzaldehyde)

In a 100 ml reactor containing argon gas, 2 g of 4,4'-oxybis(toluene) (CAS Registration No. 1579-40-4) [10 mmol] is dissolved in 39.2 ml of acetonitrile, with the addition of 0.8 ml of dimethyl sulfoxide [11.2 mmol] at 75° C. To the solution, 60 mg of $Cu(OAc)_2$, 30 mg of $FeSO_4.7H_2O$ and 10 ml of water are added. Next, while stirring forcefully, 10.8 g of $Na_2S_2O_8$, dissolved in 30 ml of water, are then added drop by drop. The reaction is ended after 45 minutes. The organic phase is extracted to exhaustion with ethyl acetate. The products formed are analyzed using HPLC.

The yield of the dialdehyde 4,4'-oxybis(benzaldehyde) (CAS Registration No. 2215-76-1) is 87 mol %. Thus compared to the yields with previously known oxidation methods, of 30 to 40%, this yield is substantially higher, making the selectivity of the method of the invention excellent.

EXAMPLE 2

Production of 4,4'-(1-methylethane-1,1-diyl)-bis (benzaldehyde)

In a 100 ml reactor containing argon gas, 2.24 g of 1,1'-(1-methylethane-1,1-diyl)-bis-(4-methylbenzene) (CAS Registration No. 1823-31-0) [10 mmol] is dissolved in 39.2 ml of acetonitrile, with the addition of 0.8 ml of dimethyl sulfoxide [11.2 mmol] at 75° C. To the solution, 60 mg of $Cu(OAc)_2$, 30 mg of $FeSO_4.7H_2O$ and 10 ml of water are added. Next, while stirring forcefully, 10.8 g of $Na_2S_2O_8$, dissolved in 30 ml of water, are then added drop by drop. The reaction is ended after 100 minutes. The organic phase is extracted to exhaustion with ethyl acetate.

The yield of the dialdehyde 4,4'-(1-methylethane-1,1-diyl)-bis(benzaldehyde) (CAS Registration No. 46948-52-1) is 86% (area) HPLC.

EXAMPLE 3

Production of biphenyl-4,4'-dicarbaldehyde

In a 100 ml reactor containing argon gas, 1.82 g of 4,4'-dimethylbiphenyl (CAS Registration No. 613-33-2) [10 mmol] is dissolved in 39.2 ml of acetonitrile, with the addition of 0.8 ml of dimethyl sulfoxide [11.2 mmol] at 70° C. To the solution, 60 mg of $Cu(OAc)_2$, 50 mg of $FeSO_4.7H_2O$ and 10 ml of water are added. Next, while stirring forcefully, 11.8 g of $Na_2S_2O_8$, dissolved in 30 ml of water, are then added drop by drop. The reaction is ended after 250 minutes. The organic phase is extracted to exhaustion with ethyl acetate. The products formed are analyzed using ethyl acetate.

The yield of the biphenyl-4,4'-dicarbaldehyde (CAS Registration No. 66-98-8) is 85 mol %.

EXAMPLE 4

Production of 4-methoxybenzaldehyde

In a 100 ml reactor containing argon gas, 2.44 g of 1-methoxy-4-methylbenzene (CAS Registration No. 104-93-8) [20 mmol] is dissolved in 39 ml of acetonitrile, with the addition of 1.0 ml of dimethyl sulfoxide [14.1 mmol] at 70° C. To the solution, 65 mg of Cu(OAc)$_2$, 30 mg of FeSO$_4$.7H$_2$O and 10 ml of water are added. Next, while stirring forcefully, 11.0 g of Na$_2$S$_2$O$_8$, dissolved in 30 ml of water, are then added drop by drop. The reaction is ended after 120 minutes.

The yield of the monoaldehyde 4-methoxybenzaldehyde (CAS Registration No. 123-11-5) is 92 mol %.

EXAMPLE 5

Production of 4,4'-oxybis(benzaldehyde)

In a 100 ml reactor containing argon gas, 2 g of 4,4'-oxybis(toluene) (CAS Registration No. 1579-40-4) [10 mmol] is dissolved in 39.2 ml of acetonitrile, with the addition of 0.9 ml of dimethyl sulfide [11.0 mmol] at 75° C. To the solution, 60 mg of Cu(OAc)$_2$, 30 mg of FeSO$_4$.7H$_2$O and 10 ml of water are added. Next, while stirring forcefully, 16.2 g of Na$_2$S$_2$O$_8$, dissolved in 30 ml of water, are then added drop by drop. The reaction is ended after 65 minutes. The organic phase is extracted to exhaustion with ethyl acetate.

The yield of the dialdehyde 4,4'-oxybis(benzaldehyde) (CAS Registration No. 2215-76-1) is 84 mol %.

EXAMPLE 6

Production of 4,4'-oxybis(benzaldehyde)

In a 100 ml reactor containing argon gas, 2 g of 4,4'-oxybis(toluene) (CAS Registration No. 1579-40-4) [10 mmol] is dissolved in 39.2 ml of acetonitrile, with the addition of 1.5 ml of methylphenyl sulfoxide [11.0 mmol] at 75° C. To the solution, 60 mg of Cu(OAc)$_2$, 30 mg of FeSO$_4$.7H$_2$O and 10 ml of water are added. Next, while stirring forcefully, 10.8 g of Na$_2$S$_2$O$_8$, dissolved in 30 ml of water, are then added drop by drop. The reaction is ended after 45 minutes. The organic phase is extracted to exhaustion with ethyl acetate.

The yield of the dialdehyde 4,4'-oxybis(benzaldehyde) (CAS Registration No. 2215-76-1) is 84 mol %.

The invention claimed is:

1. A method for the production of aliphatic and aromatic carbonyl compounds having at least one aldehyde or ketone function, and these compounds may also simultaneously have at least one aldehyde and ketone function, wherein at least one starting material, which has at least one aliphatically and/or aromatically bonded functional group of formula I

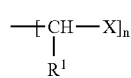

(I)

in which R$^1$ stands for hydrogen, alkyl or aryl, X stands for hydrogen or a group that can be substituted during the catalytic reaction for the sulfinyl group of a sulfoxide, and n stands for integral values between 1 and 8, is oxidized, in the presence of at least one sulfoxide and/or at least one sulfide in the simultaneous presence of iron salts or redox pairs of iron-copper or silver-copper salts, by means of at least one oxidant having a redox potential of $E_0 \geq +2$ V vs. NHE, the sulfoxide and/or the sulfide being used in a catalytic function.

2. The method according to claim 1, wherein for the production of aliphatic and aromatic mono- and polyaldehydes, at least one starting material is oxidized that has at least one aliphatically and/or aromatically bonded functional group of formula I, in which R$^1$ stands for hydrogen.

3. The method according to claim 1, wherein for the production of aliphatic and aromatic mono- and polyketones, at least one starting material is oxidized that has at least one aliphatically and/or aromatically bonded functional group of formula I, in which R$^1$ stands for alkyl or aryl.

4. The method according to claim 1, wherein for the production of carbonyl compounds that have both aliphatically or aromatically bonded aldehyde and aliphatically or aromatically bonded ketone functions, at least one starting material is oxidized which has at least one aliphatically and/or aromatically bonded functional group of formula I, in which R$^1$ stands for hydrogen in the formation of aldehyde functions and stands for alkyl or aryl in the formation of ketone functions.

5. The method according to claim 1, wherein as sulfoxides, dialkyl, diaryl, or alkylaryl sulfoxides are used, and that as sulfides, dialkyl, diaryl, or alkylaryl sulfides are used.

6. The method according to one claim 1, wherein at least one sulfoxide and/or at least one sulfide is used in the reaction mixture.

7. The method according to claim 1, wherein the at least one sulfoxide and/or the at least one sulfide is dissolved in the reaction mixture.

8. The method according to claim 1, the wherein at least one sulfoxide and/or the at least one sulfide is immobilized on a solid body, and this body is made into a slurry in the reaction mixture.

9. The method according to claim 1, the wherein at least one sulfoxide and/or the at least one sulfide is used with a mole fraction of 1 to 90 mol %, referred to the aldehyde or ketone function formed.

10. The method according to claim 1, the wherein at least one sulfoxide and/or the at least one sulfide is used with a mole fraction of 1 to 500 mol %, referred to the aldehyde or ketone function formed.

11. The method according to claim 1, wherein the oxidant is used in the form of powder or in an aqueous solution.

12. The method according to claim 1, wherein persulfate salts or a mixture thereof is used as the oxidant.

13. The method according to claim 12, wherein alkali persulfate or ammonium persulfate is used as the persulfate salts.

14. The method according to claim 1, wherein water-soluble iron salts, preferably selected from the group comprising sulfates, nitrates and acetates, are used either alone or in a mixture with water-soluble copper salts.

15. The method according to claim 1, wherein water-soluble silver salts, preferably selected from the group comprising sulfates, nitrates and acetates, are used either alone or in a mixture with water-soluble copper salts.

16. The method according to claim 1, wherein water-soluble copper salts, preferably selected from the group comprising sulfates, nitrates and acetates, are used either alone or in a mixture with iron salts or silver salts.

17. The method according to claim 1, wherein iron salts or silver salts are used in the redox pairs in concentrations of from 0.005 to 10 mol %, referred to the starting material to be oxidized, and that the copper salt is used in a molar ratio of Fe:Cu or Ag:Cu of from 0.1 to 3.

18. The method according to claim 1, wherein the oxidation is performed in an inert reaction medium selected from the group comprising water, organic solvent, and a mixture thereof.

19. The method according to claim 18, wherein as the organic solvent, acetonitrile, methyl and ethyl alcohol, acetone, acetic acid, dimethyl formamide, or acetamide is used.

20. The method according to claim 1, wherein the oxidation is performed at a temperature of from 10 to 100° C.

* * * * *